Aug. 18, 1959 M. ROBICHON Plant Pat. 1,859
ROSE PLANT
Filed Dec. 10, 1958
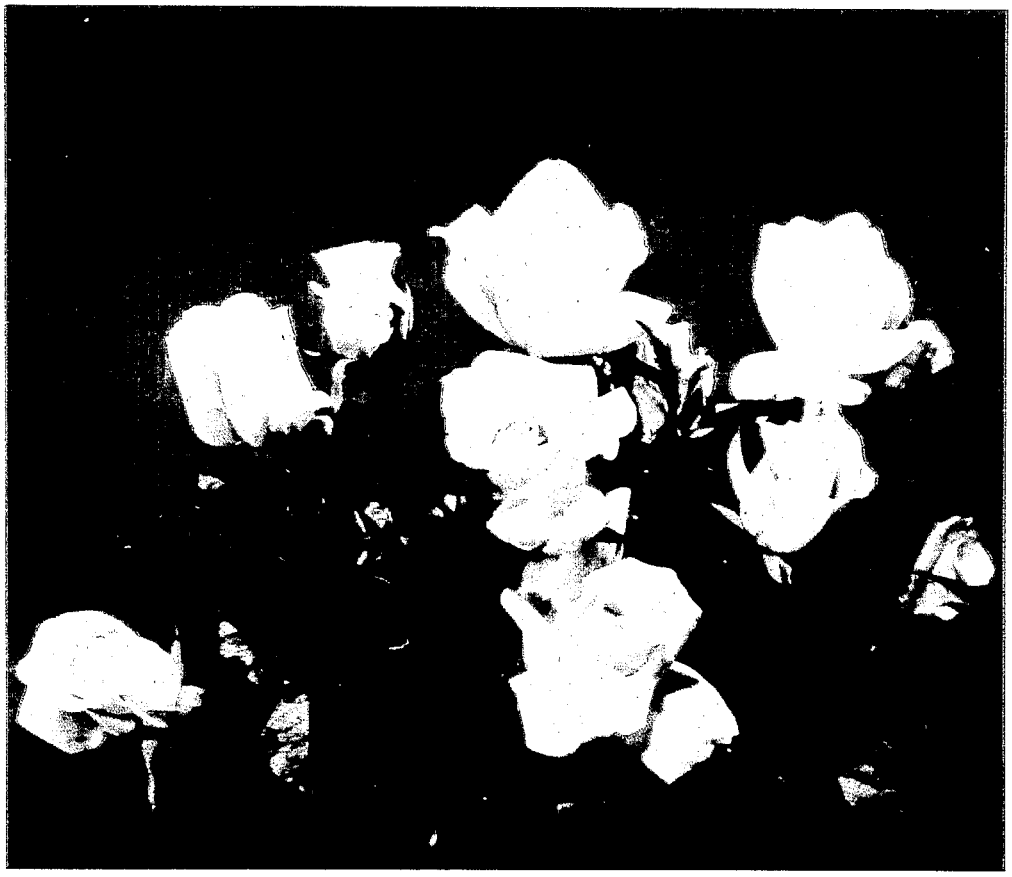
Inventor.
Marcel Robichon
By: Robb & Robb
Attorneys.

United States Patent Office

Plant Pat. 1,859
Patented Aug. 18, 1959

1,859

ROSE PLANT

Marcel Robichon, Pithiviers, Loiret, France, assignor to Ilgenfritz Nurseries, Inc., Monroe, Mich., a corporation of Michigan Application December 10, 1958, Serial No. 779,512

1 Claim. (Cl. 47—61)

The present invention relates to a new and distinct variety of rose plant of the hybrid tea class, which was originated by me by crossing the variety "Helen Fox" (unpatented) with an unnamed and unpatented seedling derived from a cross of "Mrs. Pierre S. Dupont" (unpatented×"Joanna Hill" (unpatented).

As the result of this breeding, I have produced a new variety of rose plant which is distinguished from its parents, as well as from all other varieties of its class of which I am aware, and which is particularly characterized as to novelty by the unique combination of the following outstanding features:

(1) Glossy foliage of distinctive shape and color;
(2) A compact habit of bloom; and
(3) A distinctive yellow general color tonality of the blooms which persists without appreciably fading from the bud stage to the fully open flowers.

Asexual reproduction of my new variety by budding, as performed in France, as well as at Monroe, Michigan, U.S.A., shows that the foregoing characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character.

The following is a detailed description of my new variety, with color terminology in accordance with The Horticultural Colour Chart issued by The British Colour Council in collaboration with The Royal Horticultural Society, except where general color terms of ordinary dictionary significance are obvious:

Type: Half-hardy; dwarf; bush; outdoor; seedling; for cut flowers and for garden decoration.
Class: Hybrid tea.
Breeding: Seedling.
*Seed parent.*—"Helen Fox."
*Pollen parent.*—An unnamed seedling derived from a cross of "Mrs. Pierre S. Dupont"×"Joanna Hill."
Propagation: Holds its distinguishing characteristics through succeeding propagations by budding.

*Flower*

Locality where grown and observed: Monroe, Michigan, U.S.A.
Continuity: Continuous.
Fragrance: Strong. Nature—tea.
Flowers borne: Singly; on strong stems of medium length.
Quantity of bloom: Free, outdoors.
Bud:
*Peduncle.*—Medium length; medium caliper; erect; stiff; entire; with red prickles. Color—green-bronze.
*Before calyx breaks.* — Size — medium. Form—pointed; with foliaceous appendages on the surface of the bud; with much-cut foliaceous parts extending beyond the tip of the bud equal to ¼ or more of its length. Color—Scheeles Green, Plate 860/3.
*As calyx breaks.*—Color—Sulphur Yellow, Plate 1/2.
*As first petal opens.*—Size—medium. Form—long; pointed. Color: outside—Sulphur Yellow, Plate 1/2; inside—Barium Yellow, Plate 503.
*Opening.*—Opens up well.

Bloom:
*Size (when fully open).*—Medium; from 3 inches to 3½ inches.
*Petalage.*—Double. Average number of petals under normal conditions—from 28 to 30.
*Form.*—Full and high-centered at first, but becoming open and high-centered; petals being at first tightly rolled outward, but later becoming very loosely rolled outward at maturity.
Petals:
*Appearance.*—Inside—velvety. Outside—velvety.
*Shape.*—Outside—obovate; scalloped; with 1 notch. Intermediate—obovate, with 1 notch. Inside—obovate; scalloped.

This description of a newly opened flower was made from a rose grown outdoors in the month of June at Monroe, Michigan, U.S.A.

*Color.*—Outer petal: outside surface—Aureolin Yellow, Plate 3/1 at base, shading to Aureolin Yellow, Plate 3/2 at tip; inside surface—Aureolin Yellow, Plate 3 at base, shading to Aureolin Yellow, Plate 3/2 at tip. Intermediate petal: outside surface—Aureolin Yellow, Plate 3/1 at base, shading to Aureolin Yellow, Plate 3/2 at tip; inside surface—Aureolin Yellow, Plate 3 at base, shading to Aureolin Yellow, Plate 3/2 at tip. Inner petal: outside surface—Aureolin Yellow, Plate 3/1; inside surface—Aureolin Yellow, Plate 3 at base, shading to Aureolin Yellow, Plate 3/2 at tip.

This description was made from a rose that was open for 3 days outdoors in the month of June at Monroe, Michigan, U.S.A.:

*Color.*—Outer petal: outside surface—Barium Yellow, Plate 503; inside surface—Canary Yellow, Plate 2/1 at base, shading to Canary, Plate 2/2 at tip. Inner petal: outside surface—Barium Yellow, Plate 503/1; inside surface—Canary Yellow, Plate 2/2.
*General color effect.*—Newly opened flower—Canary Yellow, Plate 2/2. 3-days open—Canary Yellow, Plate 2/2.
*Behavior.*—Drop off cleanly.
*Flower longevity.*—On bush in garden—5 days in June. Cut roses grown outdoors and kept at living-room temperatures—6 days in June.

*Reproductive organs*

Stamens: Many; irregularly arranged about pistils; mixed with petaloids.
Filaments: Long; most with anthers. Color—yellow.
Anthers: Medium size; all open at once. Color—light brown.
Pollen: Sparse. Color—gold.
Pistils: Few.
Styles: Even; very short; medium caliper; bunched.
Stigma: Color—yellow.
Ovaries: All enclosed in calyx.
Hips: Short; globular; hairy; walls thin and dry. Color—green.
Sepals: Permanent; spear-shaped. Color—grey-green.
Seeds: Many; small.

*Plant*

Foliage:

*Leaves.*—Compound of 5 leaflets; normal abundance; medium size; heavy; glossy.

*Leaflets.*—Shape—oval, with apex acute. Margin—simply serrate.

*Color.*—Mature: upper surface—normal green; under surface—light green. Young: upper surface—light green; under surface—red-green.

*Rachis (the supporting stem of the compound leaf).*—Medium caliper. Upper side—grooved; prickly. Under side—prickly.

*Stipules.*—Medium length; narrow; with very long points turning out at an angle of less than 45°.

*Disease resistance.*—Resistant to mildew and black-spot, as determined by comparison with other varieties grown under comparable cultural conditions at Monroe, Michigan, U.S.A.

Growth:

*Habit.*—Upright.

*Growth.*—Vigorous.

*Canes.*—Medium caliper.

*Main stems.*—Color—dull green. Thorns—few; straight; with long, narrow base. Prickles—none. Hairs—none.

*Branches.*—Color—dull green. Thorns—few; with long, narrow base. Prickles—few; color—reddish. Hairs—none.

*New shoots.*—Color—bright bronze. Thorns—few; straight; with long, narrow base. Prickles—few; color—reddish. Hairs—none.

I claim:

A new and distinct variety of rose plant of the hybrid tea class, substantially as herein shown and described, characterized particularly as to novelty by the unique combination of glossy foliage of distinctive shape and color, a compact habit of bloom, and a distinctive yellow general color tonality of the blooms which persists without appreciably fading from the bud stage to the fully open flowers.

No references cited.